United States Patent
Bell

(10) Patent No.: US 11,260,045 B2
(45) Date of Patent: Mar. 1, 2022

(54) METHOD OF MAXIMIZING EPIGALLOCATECHIN GALLATE CONTENT IN TEA

(71) Applicant: Rory Bell, Dieppe (CA)

(72) Inventor: Rory Bell, Dieppe (CA)

(73) Assignee: MILLENNIA TEA INC., Rothesay (CA)

( * ) Notice: Subject to any disclaimer, the term of this patent is extended or adjusted under 35 U.S.C. 154(b) by 574 days.

(21) Appl. No.: 15/932,035

(22) Filed: Jan. 26, 2018

(65) Prior Publication Data
US 2019/0231738 A1   Aug. 1, 2019

(51) Int. Cl.
*A61K 31/353* (2006.01)
*A61K 36/82* (2006.01)
*A23F 3/18* (2006.01)

(52) U.S. Cl.
CPC ............. *A61K 31/353* (2013.01); *A23F 3/18* (2013.01); *A61K 36/82* (2013.01); *A61K 2236/10* (2013.01); *A61K 2236/11* (2013.01); *A61K 2236/331* (2013.01)

(58) Field of Classification Search
None
See application file for complete search history.

(56) References Cited

U.S. PATENT DOCUMENTS 5,993,867 A * 11/1999 Rohdewald ............. A61P 43/00
426/96
7,815,960 B2 * 10/2010 Quan ...................... A23F 3/163
426/597

FOREIGN PATENT DOCUMENTS

CA     2552884 A1     7/2005

OTHER PUBLICATIONS

Green (Mol. Nutr. Food Res. (2007), vol. 51, pp. 1152-1162).*
"Tea Source" (https://www.teasource.com/blogs/beyond-the-leaf/tagged/behind-the-scenes?page=2—posted Nov. 21, 2014; accessed Feb. 2021).*

* cited by examiner

*Primary Examiner* — Susan Hoffman
(74) *Attorney, Agent, or Firm* — Bereskin & Parr LLP/S.E.N.C.R.L., s.r.l.; Micheline Gravelle

(57) ABSTRACT

This invention describes a new method to maximize the epigallocatechin gallate (EGCG) content of brewed tea made using leaves and buds from *C. sinensis*. Unlike conventional tea processing methods, the method of the invention aims to minimize the leaf withering step, the oxidation step and any heating steps, all of which are present in many conventional tea processing methods. The method of the invention treats minimally withered tea leaf and bud material with an acid treatment and then a maceration treatment, optionally freezing the acid-treated material for storage purposes. The brewed tea resulting from the acid-treated and macerated leaves has a significantly higher EGCG content than conventionally produced teas.

8 Claims, No Drawings

METHOD OF MAXIMIZING EPIGALLOCATECHIN GALLATE CONTENT IN TEA

FIELD OF THE INVENTION

This invention relates generally to novel methods of maximizing the extraction of catechins from brewed tea. More specifically, this invention relates to the maximization of epigallocatechin gallate (EGCG) levels in tea made from *Camellia sinensis*.

BACKGROUND

The current invention has application to the field of tea brewing and consumption. Tea is produced from the *Camellia sinensis* plant, a species of evergreen shrub or small tree. Two major varieties of *C. sinensis* are grown: *C. sinensis* var. *sinensis*, and *C. sinensis* var. *assamica*. The former is used to produce Chinese teas, while the latter is used to produce Indian Assam teas. Forms of tea produced from these varieties of *C. sinensis* include green, white, yellow, black, oolong, pu-erh and matcha tea. Most of the teas are produced with the leaves exclusively, although some forms of tea also include the twigs and stems.

Some forms of tea do not contain any *C. sinensis*, including many herbal and fruit infusions. This invention does not pertain to teas that do not contain *C. sinensis* materials. For the purpose of this disclosure, the term "tea" includes only those beverages produced with material from *C. sinensis*.

For the purpose of this invention, the term "brewed tea" refers to a tea-based beverage that results from allowing the *C. sinensis* plant material to steep in water in order to extract the flavor and chemical compounds from the tea. In general, tea is brewed or steeped using hot water, most typically boiling water or water that is close to the boiling point. Some tea is also "sun tea" that is allowed to brew at ambient temperatures in sunlight. Tea can also be brewed using cold water over a longer period of time, optionally in a refrigerated environment. Any method of combining tea leaves with water to produce a beverage is considered to be "brewed tea" for the purposes of this disclosure. The time that the leaves are allowed to remain in the water can vary from a few seconds up to many hours, depending on the techniques used and the desired strength of the beverage.

*C. sinensis* is native to East Asia, Southeast Asia, and the Indian Subcontinent. Today, it is cultivated around the world in tropical and subtropical regions. The plant is usually kept trimmed to less than 2 metres in height in order to facilitate picking. Tea leaves are typically harvested several times during the harvesting season, which begins in March and carries through to November in the Northern Hemisphere. In countries south of the equator, the harvesting season runs October to May. Picking tea typically involves picking a terminal bud and two young leaves. Picking can be done mechanically or by hand.

After picking, the leaves of *C. sinensis* begin to wilt and oxidize unless they are heated immediately. Typically, the enzymatic oxidation reaction in the leaves that causes darkening and release of tannins is halted by heating, often simultaneously as the leaves are dried. Tea is conventionally dried for ease of packaging, shipping and storage.

All teas produced from *C. sinensis* contain a number of chemical compounds including caffeine, theobromine, theophylline, and polyphenols. Among the polyphenols are flavonoids and catechins. Flavanols (also called flavan-3-ols) are derivatives of flavans that use the 2-phenyl-3,4-dihydro-2H-chromen-3-ol skeleton. The compounds from tea that fall into this group include catechin (C), epicatechin gallate (ECG), epigallocatechin (EGC), epigallocatechin gallate (EGCG), epicatechin (EC), and catechin gallate (CG). C and EC are epimers, while EGC and gallocatechins contain an additional phenolic hydroxyl group when compared to C and EC. EGCG and EGC are the most abundant catechins in green tea (Williamson et al. (2011) *Mol. Nutr. Food. Res.* 55:864-873).

The catechins contained in tea have recently been of increasing interest due to their strong antioxidant effect, as described in, for example, Zhao B. et. al. (1989), Cell Biophys. 14, 175, which outlines the scavenging effects of the catechins on active oxygen radicals, and Huang M. T. et al., (1992) Carcinogenesis 13, 947, which outlines the inhibition of tumor initiation and promotion in mouse skin as a result of topical application of catechins.

In addition, research is increasingly demonstrating a cancer chemo-preventive effect of catechins. Singh et al. (2014) *Biochem Pharmacol*. 82(12): 1807-1821 review a broad range of studies showing that EGCG performs as a powerful antioxidant, preventing oxidative damage in healthy cells and acting as an antiangiogenic and antitumor agent. In addition, Singh mentions the benefits of EGCG in early studies in diabetes, Parkinson's disease, Alzheimer's disease, stroke and obesity.

Given the increasing interest in tea catechins, and EGCG in particular, there is a need for methods of maximizing the EGCG content of tea in order to take full advantage of its beneficial properties.

SUMMARY OF THE INVENTION

Provided is a method of maximizing EGCG content from tea. In one embodiment, the content of EGCG is maximized by harvesting tea leaf and bud material from *C. sinensis*, minimizing the withering time of said leaf and bud material, treating the leaf and bud material with an acid treatment, infusing the treated material in water, and macerating the treated, infused material to produce a final tea product with higher EGCG content.

The acid treatment may comprise ascorbic and citric acid and may be obtained from citrus fruits or other sources of ascorbic and/or citric acid.

Optionally, the treated tea leaf and bud material may be subjected to a carefully controlled freezing step in order to maintain shelf life and stability of the EGCG levels within the product. The infusion and maceration may optionally occur after the freezing step.

DETAILED DESCRIPTION

The following is a detailed description of an embodiment of technology and methods enabling improved catechin levels in tea produced from *C. sinensis*, and in particularly, improved EGCG levels in tea produced from *C. sinensis*.

Following the picking of tea leaves, the leaves begin to wilt and oxidize. This is desirable in tea because it causes the leaves to turn darker as they produce tannins, which create the characteristic flavor of tea. The withering process is carefully controlled by tea producers by monitoring of the humidity, temperature, and air flow around the leaves. It is desirable for the leaves to wither evenly. The darkening, and tannin production, are typically stopped during the drying of the tea, by heating. The ending of the withering process is typically governed by the amount of water loss, usually measured by percent, and usually a moisture reduction of one third to one half is normal. Further moisture reduction occurs later in the conventional tea processing cycle.

In the present application, it is recommended to allow the leaves to wither for a period of fewer than 16 hours. The withering time can optionally be eliminated entirely by processing using a mobile in-field unit to begin processing the leaves immediately. Alternatively, withering can be carried out for a short time, such as a few minutes, 5 minutes, 10 minutes, 15 minutes, 30 minutes, 45 minutes, or up to an hour. Withering can also be carried out for a longer time, including 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, or any period of time up to 16 hours. Withering can be achieved using standard techniques known in the art of tea production. The working examples described later in this application use a period of 7 hours for withering. This period was chosen as the average time frame for the leaves to proceed from picking to processing in an average tea harvesting operation.

The withering process reduces the level of catechins in tea, as demonstrated by Chen. (Chen, C. (1984) Theory in Tea Processing, 51-52, 205-217, Shanghai: Shanghai Science and Technology Press.) As seen in Table 1, below, the catechins in white tea drop significantly during the withering process.

TABLE 1

The variation of catechins (in mg) of white tea during processing

| Catechin | Fresh Leaves | Withering 8 hours | Withering 16 hours | Withering 32 hours |
|---|---|---|---|---|
| EGC | 36.70 | 24.54 | 19.62 | 8.61 |
| GC | 23.74 | 16.56 | 11.42 | 4.91 |
| EC + C | 24.32 | 20.76 | 15.20 | 10.51 |
| EGCG | 122.56 | 90.08 | 77.02 | 55.49 |
| ECG | 40.62 | 31.89 | 26.31 | 20.21 |
| Total | 247.94 | 183.83 | 149.57 | 109.73 |

During the withering process, oxidation begins to occur inside the tea leaves. Chlorophyll in the tea leaves is degrading, while flavor compounds begin to accumulate. The cell walls of the individual leaf cells begin to break down, which initiates the activity of polyphenol oxidase and peroxidase. These compounds cause oxidation of the cell contents. Some components of the leaves will degrade into volatile components. During oxidation, the catechins, which are located in the leaf cell vacuoles, are converted into flavonoids—specifically theaflavins and thearubigins. These compounds provide the tea with taste and colour. However, this process also reduces the level of catechins because they are being converted into other compounds. Therefore, it is permissible to allow some oxidation for the purpose of flavor, but ideally, the time from picking to freezing should be minimized in order to prevent oxidation, thereby retaining the maximum level of catechins while not completely compromising flavor profiles.

Oxidation in standard tea production requires careful control of humidity and oxygen. Oxidation occurs best at a temperature range of 26.7 to 29.4° 14 C (80 to 85° F.), and is slowed almost completely at a range of 60 to 65.5° C. (140 to 150° F.) (Basu & Ullah (1978) Two and A Bud 25(1): 7-11). For the purposes of this invention, no oxidation, or very limited oxidation is desirable because more of the catechins are left intact. When oxidation is allowed to continue in the leaves, many of the catechins will have been converted, leaving far fewer catechins in the final tea. Thus, unlike in conventional tea processing, the leaves used to produce tea according to this disclosure are not subjected to a specific oxidation step.

The oxidation process in standard tea production is typically stopped by heating the leaves. This is also referred to as fixing or kill-green. To stop oxidation, the leaves must be heated to a minimum of 65.5° C. (150° F.). Numerous methods can be used to heat the leaves, including steaming, pan firing, boiling, heated tumbling, heated drying in ovens or similar units, and sun drying, which results in fixing as a result of dehydration rather than heating. Because of the intent to maximize catechins, the disclosed invention does not use a heated fixing step. The intent of the invention is to take the leaves from the picking step to the freezing step as quickly as possible by minimizing any withering and also minimizing any oxidation. The tea leaves in the present invention are subjected to freezing as soon as possible after picking. Unlike in conventional tea processing, in the present disclosure, the combination of the acid treatment and subsequent freezing process acts as a fixing step.

In general, tea leaves are dried as a final step in their processing. Drying is a convenient and relatively simple way to keep tea leaves shelf-stable and the process also makes the leaves easier to transport and store. Drying can also potentially enhance the flavor of the tea. Drying is typically achieved using a commercial dryer such as a heater or fluidized bed dryer, an oven, or sun drying. Less common methods include charcoal firing or drying on a heated floor. Drying typically aims to reduce moisture levels to 2-3%, slowing oxidative processes almost completely and making the leaves shelf stable. Unlike conventional tea processing, in the present disclosure, prolonged drying is not a desirable step because it will reduce catechin levels.

Tea leaves are conventionally dried to approximately one quarter of their original weight. Typically, 10 grams of leaves/buds are reduced to 2.5 grams, which is used for a typical 250 mL serving of brewed tea. Often, tea is dried to a point that it contains one to six percent moisture content. Contrary to traditional tea drying methods, the present disclosure aims to avoid such drying. The present disclosure aims to produce a tea from leaves that retain 50 to 100% of their original moisture content at the time of picking. This is achieved by the minimal withering time and subsequent treatment of the leaf and bud material. Shorter withering times result in higher levels of EGCG and other catechins.

Ascorbic acid has previously been demonstrated to stabilize catechins in green tea (Chen et al. (1998) J. Agric. Food Chem. 46(7): 2512-2516). Chen showed that while catechins are typically unstable and degraded quickly, the addition of acid would increase their stability. Chen demonstrated that adding ascorbic acid to catechins in a sodium phosphate buffer improved their stability for up to 20 hours.

By using a lemon juice treatment on the harvested and withered tea leaves, thereby providing an acid treatment, the instant invention demonstrates a significant increase in catechin levels. In addition, applicants have demonstrated that the maceration of a lemon-treated sample of tea leaves, coupled with a second infusion, results in 79 times the level of EGCG than a typically-processed tea sample. This increase is surprisingly high in comparison with typically processed teas.

The following examples illustrate the present invention in more detail and are illustrative of how the invention described herein could be implemented in tea. The initial steps of Example were conducted in North Carolina and the analysis was subsequently conducted in Quebec, Canada. Testing was conducted in October and November of 2016.

Example 1: Preparation of Samples

The invention described herein was practiced using *C. sinensis* var. *sinensis* leaf obtained from a nursery in North Carolina. Two leaves and a bud were picked from three-year old plants. The total amount picked was between 70 and 80 grams of plant material. The leaves were allowed to wither naturally on a bamboo rack for seven hours.

The gathered, withered plant material was divided into 6 separate samples. One sample gave inconclusive results, and another sample was not ultimately tested, so only four samples will be reviewed in this example.

The four samples were subjected to different treatments as shown in Table 2, below.

TABLE 2

Sample Treatments

| # | Name | Treatment Methodology |
|---|------|----------------------|
| 1 | Steamed | 10 grams of plant material was steamed in a bamboo steaming rack with a lid over 95° C. boiling water for 40 seconds, then vacuum sealed in plastic and rapidly frozen in controlled conditions at −27° C. using dry ice. |
| 2 | Processed | 10 grams of plant material was steamed in a bamboo steaming rack with a lid over 95° C. boiling water for 45 seconds, then left to dry on the bamboo rack to wither for 30 minutes at a temperature of 65° C., and vacuum-sealed. Post-drying weight was 2.6 grams. |
| 3 | Lemon-treated | 10 grams of plant material was bathed in approximately 6 tablespoons of freshly-squeezed lemon juice for 10 seconds. The bathing step was accomplished using a glass jar, and the leaves were stirred within the lemon juice and were removed from the bath using a strainer. The sample was then vacuum-sealed and rapidly frozen in controlled conditions at −27° C. using dry ice. |
| 4 | Natural | 10 grams of plant material was vacuum-sealed and rapidly frozen in controlled conditions at −27° C. using dry ice. |

Samples 1, 3 and 4 were transported on dry ice and shipped to a testing facility in Quebec, Canada. Sample 2 was shipped to the same testing facility but, because it was not frozen, it was treated in the same manner as conventional finished tea and was therefore transported at ambient temperature.

Example 2: Infusion Testing

The treated leaves described in Example 1 were subjected to two infusions. Each sample was infused in 250 mL of 95° C. (203° F.) water for a duration of four minutes. Then the liquid was drained and a second 250 mL of 95° C. (203° F.) water was added to the same leaves for a second infusion. Samples 1, 2 and 4 had the liquid drained for testing. Sample 3 was subjected to a further step of blending for 2 minutes in a blender following the second, 6-minute infusion, and then the final liquid was filtered prior to testing.

The results for each of the four samples are provided in Tables 3 through 6, below.

TABLE 3

Results for Sample 1: Steamed

| Analysis | Method | Infusion | Result |
|----------|--------|----------|--------|
| Epigallocatechin (EGC) | UPLC-MS | 1 | 4 072 µg/10 g tea |
| | | 2 | 5 826 µg/10 g tea |

TABLE 3-continued

Results for Sample 1: Steamed

| Analysis | Method | Infusion | Result |
|----------|--------|----------|--------|
| Catechin (C) | UPLC-MS | 1 | 673 µg/10 g tea |
| | | 2 | 1 288 µg/10 g tea |
| Epicatechin (EC) | UPLC-MS | 1 | 2 580 µg/10 g tea |
| | | 2 | 3 037 µg/10 g tea |
| Epigallocatechin gallate (EGCG) | UPLC-MS | 1 | 6 170 µg/10 g tea |
| | | 2 | 9 387 µg/10 g tea |
| Epicatechin gallate (ECG) | UPLC-MS | 1 | 3 180 µg/10 g tea |
| | | 2 | 3 256 µg/10 g tea |
| Catechin gallate (CG) | UPLC-MS | 1 | 560 µg/10 g tea |
| | | 2 | 927 µg/10 g tea |
| Caffeine | HPLC-UV | 1 | 40 mg/10 g tea |
| | | 2 | 17 mg/10 g tea |
| H-ORAC | USDA Spectrofluorimetry | 1 | 5 131 TEAC [1] |
| | | 2 | 6 806 TEAC [1] |
| H-ORAC | USDA Spectrofluorimetry | 1 | 513 µmol/250 mL tea [2] |
| | | 2 | 513 µmol/250 mL tea [2] |

[1] TEAC: Trolox Equivalent Antioxidants Capacity. Results expressed in µmol TE/100 g of sample.
[2] Units to compared *Camellia sinensis* results

TABLE 4

Results for Sample 2: Processed

| Analysis | Method | Infusion | Result |
|----------|--------|----------|--------|
| Epigallocatechin (EGC) | UPLC-MS | 1 | 3034 µg/2.6 g tea |
| | | 2 | 383 µg/2.6 g tea |
| Catechin (C) | UPLC-MS | 1 | 1278 µg/2.6 g tea |
| | | 2 | 1596 µg/2.6 g tea |
| Epicatechin (EC) | UPLC-MS | 1 | 3541 µg/2.6 g tea |
| | | 2 | 2760 µg/2.6 g tea |
| Epigallocatechin gallate (EGCG) | UPLC-MS | 1 | 5318 µg/2.6 g tea |
| | | 2 | 1201 µg/2.6 g tea |
| Epicatechin gallate (ECG) | UPLC-MS | 1 | 3363 µg/2.6 g tea |
| | | 2 | 2979 µg/2.6 g tea |
| Catechin gallate (CG) | UPLC-MS | 1 | 905 µg/2.6 g tea |
| | | 2 | 1160 µg/2.6 g tea |
| Caffeine | HPLC-UV | 1 | 45 mg/2.6 g tea |
| | | 2 | 15 mg/2.6 g tea |
| H-ORAC | USDA Spectrofluorimetry | 1 | 27 000 TEAC [1] |
| | | 2 | 26 000 TEAC [1] |
| H-ORAC | USDA Spectrofluorimetry | 1 | 703 µmol/250 mL tea [2] |
| | | 2 | 675 µmol/250 mL tea [2] |

[1] TEAC: Trolox Equivalent Antioxidants Capacity. Results expressed in µmol TE/100 g of sample.
[2] Units to compared *Camellia sinensis* results

TABLE 5

Results for Sample 3: Lemon Treated

| Analysis | Method | Infusion | Result |
|----------|--------|----------|--------|
| Epigallocatechin (EGC) | UPLC-MS | 1 | 14 711 µg/10 g tea |
| | | 2 | 60 911 µg/10 g tea |
| Catechin (C) | UPLC-MS | 1 | 294 µg/10 g tea |
| | | 2 | 2 243 µg/10 g tea |
| Epicatechin (EC) | UPLC-MS | 1 | 4 322 µg/10 g tea |
| | | 2 | 15 281 µg/10 g tea |
| Epigallocatechin gallate (EGCG) | UPLC-MS | 1 | 20 604 µg/10 g tea |
| | | 2 | 95 156 µg/10 g tea |
| Epicatechin gallate (ECG) | UPLC-MS | 1 | 4 798 µg/10 g tea |
| | | 2 | 19 852 µg/10 g tea |
| Catechin gallate (CG) | UPLC-MS | 1 | ND [1] |
| | | 2 | ND [1] |
| Caffeine | HPLC-UV | 1 | 42 mg/10 g tea |
| | | 2 | 16 mg/10 g tea |

TABLE 5-continued

Results for Sample 3: Lemon Treated

| Analysis | Method | Infusion | Result |
|---|---|---|---|
| H-ORAC | USDA | 1 | 8 000 TEAC [2] |
|  | Spectro-fluorimetry | 2 | 37 415 TEAC [2] |
| H-ORAC | USDA | 1 | 800 μmol/250 mL tea [3] |
|  | Spectro-fluorimetry | 2 | 3 741 μmol/250 mL tea [3] |

[1] ND: Not Detected
[2] TEAC: Trolox Equivalent Antioxidants Capacity. Results expressed in μmol TE/100 g of sample.
[3] Units to compared *Camellia sinensis* results

TABLE 6

Results for Sample 4: Natural

| Analysis | Method | Infusion | Result |
|---|---|---|---|
| Epigallocatechin (EGC) | UPLC-MS | 1 | 3 750 μg/10 g tea |
|  |  | 2 | 4 119 μg/10 g tea |
| Catechin (C) | UPLC-MS | 1 | 673 μg/10 g tea |
|  |  | 2 | 1 514 μg/10 g tea |
| Epicatechin (EC) | UPLC-MS | 1 | 2 590 μg/10 g tea |
|  |  | 2 | 3 356 μg/10 g tea |
| Epigallocatechin gallate (EGCG) | UPLC-MS | 1 | 6 235 μg/10 g tea |
|  |  | 2 | 8 197 μg/10 g tea |
| Epicatechin gallate (ECG) | UPLC-MS | 1 | 2 882 μg/10 g tea |
|  |  | 2 | 4 155 μg/10 g tea |
| Catechin gallate (CG) | UPLC-MS | 1 | 583 μg/10 g tea |
|  |  | 2 | 1 225 μg/10 g tea |
| Caffeine | HPLC-UV | 1 | 35 mg/10 g tea |
|  |  | 2 | 21 mg/10 g tea |
| H-ORAC | USDA | 1 | 5 500 TEAC [1] |
|  | Spectro-fluorimetry | 2 | 8 100 TEAC [1] |
| H-ORAC | USDA | 1 | 547 μmol/250 mL tea [2] |
|  | Spectro-fluorimetry | 2 | 810 μmol/250 mL tea [2] |

[1] TEAC: Trolox Equivalent Antioxidants Capacity. Results expressed in μmol TE/100 g of sample.
[2] Units to compared *Camellia sinensis* results Reviewing the results from the tables presented above, it can easily be seen that all the frozen samples of tea produced higher levels of EGCG than Sample 2, which was dried and processed in the manner of typical tea processing. Furthermore, the dried sample exhibited a significant drop in EGCG level in the second infusion, resulting in less than 25% of the amount of EGCG recovered in the first infusion. Additionally, the frozen samples all had higher EGCG levels than the dried sample, and unlike the processed sample where the values dropped upon the second infusion, the values for ECGC were significantly higher on the second infusion for all three of the frozen samples.

The natural leaf sample EGCG levels were 221% higher than the processed sample. The steamed leaf sample EGCG levels were 238% higher than the processed sample, and 108% higher than the natural leaf sample. The lemon-treated sample had overall EGCG levels that were 1,776% higher than the processed sample, and 802% higher than the natural leaf sample. Notably, the EGCG levels on the lemon-treated sample, which were already superior to the other tested samples, nearly quadrupled following the maceration after the second infusion. The sample resulted in EGCG levels that were 7,923% higher following the second infusion and maceration than the second infusion of the processed sample, and 1160% more EGCG on the second infusion in comparison to the natural leaf sample.

Although various representative embodiments of this invention have been described above with a certain degree of particularity, those skilled in the art could make numerous alterations to the disclosed embodiments without departing from the spirit or scope of the inventive subject matter set forth in the specification and claims. In some instances, in methodologies directly or indirectly set forth herein, various steps and operations are described in one possible order of operation, but those skilled in the art will recognize that steps and operations may be rearranged, replaced, or eliminated without necessarily departing from the spirit and scope of the present invention. It is intended that all matter contained in the above description or shown in the accompanying drawings shall be interpreted as illustrative only and not limiting. Changes in detail or structure may be made without departing from the spirit of the invention as defined in the appended claims.

Although the present invention has been described with reference to the embodiments outlined above, various alternatives, modifications, variations, improvements and/or substantial equivalents, whether known or that are or may be presently foreseen, may become apparent to those having at least ordinary skill in the art. Listing the steps of a method in a certain order does not constitute any limitation on the order of the steps of the method. Accordingly, the embodiments of the invention set forth above are intended to be illustrative, not limiting. Persons skilled in the art will recognize that changes may be made in form and detail without departing from the spirit and scope of the invention. Therefore, the invention is intended to embrace all known or earlier developed alternatives, modifications, variations, improvements, and/or substantial equivalents.

The invention claimed is:

1. A method of increasing the content of epigallocatechin gallate in brewed tea, comprising
    a) harvesting tea leaf and bud material from *Camellia sinensis;*
    b) allowing said tea leaf and bud material to wither for fewer than 16 hours;
    c) treating said tea leaf and bud material with an acid treatment; and
    d) freezing said treated tea leaf and bud material,
    wherein said combined acid treatment and freezing said treated tea leaf and bud material fix said tea leaf and bud material and preserve catechins, and
    wherein said treated tea leaf and bud material retain 50 to 100% of their original moisture content at the time of picking.

2. The method of claim 1 wherein said acid treatment is a result of treatment in the juice of one or more fruits originating from the *Citrus* genus.

3. The method of claim 2 wherein said one or more fruits comprise lemon.

4. The method of claim 1, further comprises e) infusing said treated tea leaf and bud material in water.

5. The method of claim 4, further comprises f) macerating said treated tea leaf and bud material in the water to produce a brewed, macerated tea beverage.

6. The method of claim 4, wherein said infusion in water is conducted with water that has a temperature between 0 and 100 degrees Celsius.

7. The method of claim 4, wherein said water infusion step is conducted for up to 20 hours.

8. The method of claim 5, wherein said maceration step is accomplished using a tool selected from the group consisting of a blender, food processor, hand mixer, knife or other chopping instrument.

* * * * *